United States Patent [19]
Jones

[11] Patent Number: 5,249,466
[45] Date of Patent: Oct. 5, 1993

[54] ULTRASONIC TRANSDUCER FOR DETERMINING IF ANISOTROPIC STRUCTURES ARE PRESENT IN METAL

[75] Inventor: Martin P. Jones, Pittsburgh, Pa.

[73] Assignee: Aluminum Company of America, Pittsburgh, Pa.

[21] Appl. No.: 860,333

[22] Filed: Mar. 30, 1992

Related U.S. Application Data

[62] Division of Ser. No. 576,852, Sep. 4, 1990, Pat. No. 5,176,033.

[51] Int. Cl.$^5$ .............................................. G01N 29/24
[52] U.S. Cl. .......................................... 73/633; 73/644
[58] Field of Search ................ 73/597, 598, 602, 620, 73/627, 628, 632, 633, 641, 642, 644, 594, 629; 310/336

[56] References Cited

U.S. PATENT DOCUMENTS

| | | | |
|---|---|---|---|
| 3,315,520 | 4/1967 | Carnevale et al. | 73/67.5 |
| 3,504,532 | 4/1970 | Muenow et al. | 73/67.7 |
| 3,593,570 | 7/1971 | Megoloff | 73/641 |
| 4,033,182 | 7/1977 | Clotfelter | 73/88 |
| 4,080,836 | 3/1978 | Thompson et al. | 73/597 |
| 4,501,150 | 2/1985 | Rouge | 73/628 |
| 4,722,225 | 2/1988 | Hardy et al. | 73/633 |
| 4,782,702 | 11/1988 | Boone et al. | 73/597 |
| 4,790,188 | 12/1988 | Bussiere et al. | 73/597 |
| 4,912,979 | 4/1990 | Sondergeld et al. | 73/594 |

OTHER PUBLICATIONS

Yamaguchi et al., "Effects of Solute Content and Heat Treatment on Elastic Coefficients of Al-Cu Alloys Containing Columnar Crystals", Zairyoshi, vol. 32, No. 352, pp. 94–100.

R. T. Smith, "Stress-Induced Anisotropy in Solids-The Acousto-Elastic Effect", Ultrasonics/Jul.-Sep., 1963, pp. 135–147.

Primary Examiner—Hezron E. Williams
Assistant Examiner—Rose M. Finley
Attorney, Agent, or Firm—David W. Pearce-Smith

[57] ABSTRACT

A transducer unit for determining the presence of twinned columnar growth in the interior of an as-cast ingot. The transducer unit has a first means for generating and receiving ultrasonic waves and second means for rotating the direction of the wave pulse of the waves. The transducer unit detects the presence of twinned columnar growth by comparing the round trip time of flight (RTTOF) of the ultrasonic waves traveling in a first direction to ultrasonic waves of the same frequency generated in a second direction. In a preferred embodiment, a viscous liquid is used to couple the transducer unit to the ingot.

5 Claims, 2 Drawing Sheets

ULTRASONIC TRANSDUCER FOR DETERMINING IF ANISOTROPIC STRUCTURES ARE PRESENT IN METAL

This application is a division of application Ser. No. 07/576,852, filed Sep. 4, 1990, U.S. Pat. No. 5,176,033.

TECHNICAL FIELD

This invention relates to the detection of elastic anisotropy in as-formed metal. More particularly, the invention relates to nondestructive methods for the detection of twinned columnar growth (TCG) in aluminum alloys.

BACKGROUND ART

Twinned columnar growth structure is one of several internal metallurgical structures that can occur in cast alloys when solidification conditions, including grain refining additions are not optimal. Other undesirable features include, for example, columnar grains and residual stress.

Twinned columnar growth (TCG) structure in an aluminum alloy is one of the more deleterious internal structures. It is an anisotropic structure formed as a result of a highly oriented growth pattern and it results in variations of strength, ductility and elasticity of an aluminum alloy. TCG consists of many parallel continuous thin lamellae that are approximately 100 micrometers thick and several centimeters long. Each lamella comprises a twinned crystal with the twinned boundary coherent along the <111> plane and non-coherent at the edges. Growth usually occurs in the <112> direction. The variations of strength, ductility and elasticity of an aluminum alloy due to TCG is a function of the orientation of the growth direction with respect to the tensile testing direction. When the growth direction is parallel with the gauge length of the tensile specimen, strength and ductility is high. When the growth direction is oriented normal to the gauge length, strength is reduced and ductility approaches zero.

Current methods for testing for the presence of internal structural anisotropies, such as TCG, are quite expensive and time consuming. The most commonly employed methods are to scalp or surface machine the ingot, polish and then etch the exposed surface. However, these methods do not test for TCG at a depth below the scalped surface of the metal.

In addition, testing is not performed at multiple levels because multiple transverse section would be needed and there would be less metal for fabrication to a final product. As a result of current testing procedures, TCG may remain undetected until after additional time and capital has been used to work the ingot into a wrought product.

Furthermore, if TCG is detected, current techniques do not allow one to properly quantify it. The TCG found on exposed surfaces is not necessarily representative of the entire ingot. However, it is too costly to test ingots as completely as would be statistically necessary to meet rigid quality control standards. As a result, entire ingots are remelted because TCG is detected in a single portion and there is no inexpensive and nondestructive method to determine if part of the ingot is free of TCG and potentially useful for making quality product.

The present invention is directed to the use of ultrasonic waves to detect, locate and/or quantify structural anisotropies such as TCG throughout the entire cross-section of an ingot. All ultrasonic methods depend in principle upon the fact that the velocity of propagation of ultrasound (elastic waves) in a solid medium is influenced by the state of strain of the medium as well as the elastic constant as a function of direction. Although the effect of TCG on the velocity in an ingot is small, its detection and measurement are within the present state of the ultrasonic art.

However, the velocity of sound is also affected by numerous other factors related to the condition of the material such as its microstructure, heat treatment, grain orientation, density and homogeneity. Therefore, the determination of the absolute velocity of sound in a material does not give an accurate indication of stress in the material unless standards which accurately represent all the other velocity-affecting conditions are available. To overcome this problem of determining the absolute velocity determination, a known technique called shear wave birefringence is used. This technique is based upon measuring the difference in velocity of piezoelectrically generated shear waves which are orthogonally polarized by the electric field applied to the material. According to this technique, only the difference in velocity between two shear waves is measured. Since this difference in velocity is caused primarily by the difference in elastic constants in two orthogonal directions within the material, the need to know the thickness of the metal can be eliminated.

According to the prior art, piezoelectric transducers are required to generate ultrasonic waves in the material being measured. These transducers utilize an oriented crystal which is strained along a particular crystallographic axis in response to an electric field applied to the crystal (the piezoelectric effect). Consequently, the piezoelectric transducer must be rigidly attached or coupled by a very viscous fluid or a solid bond to the material being evaluated in order to inject an ultrasonic wave into the material.

Prior art that discloses the use of ultrasonic waves to determine characteristic of materials are as follows:

U.S. Pat. No. 3,315,520 issued to Carnevale et al discloses an ultrasonic measurement apparatus for determining the ultrasonic transmission characteristics of materials at elevated temperatures. The apparatus utilizes the lapse of time between generating of an ultrasonic wave at the face of the transmitting probe and the arrival of the wave at a second receiving probe to determine the velocity of the wave through the material. The method requires precise thickness measurements to calculate precise velocities. The calculated velocities are then used to determine the temperature of the material.

U.S. Pat. No. 3,504,532 issued to Muenow et al discloses a nondestructive testing system for testing the structural integrity of articles by measuring their sonic characteristics. The system includes a delay circuit which is adjusted until it produces a delay exactly equal to the time required for sound to travel a known distance from a transmitting transducer to a receiving transducer. The delay is read out as an indication of the propagation velocity of waves in the article.

U.S. Pat. No. 4,033,182 issued to Clotfelter discloses a method for measuring biaxial stress in a test articles subjected to stress inducing loads such as engineering structures and the like. The method includes obtaining the transit time differential between a second wave echo for a longitudinal wave propagated along a first path through a stressed test article and the first wave echo for at least one shear wave propagated through the article along a second path paralleling the first path, and then comparing the obtained time differential to establish a transit time differential indicative of a measurement of stress.

U.S. Pat. No. 4,080,836 issued to Thompson et al discloses a method of measuring stress in a material using electromagnetically generated, transverse elastic waves. An electromagnetic transducer is used to generate orthogonally polarized waves traveling through a test block at different velocities as a result of anisotropic stress in the part. The difference in velocity between the polarized waves is measured and compared to the correlation to obtain the stress in the existing part.

In addition, work has been performed using ultrasonic waves to determine characteristic of aluminum plate. See for example, "*Effects of Solute Content and Heat Treatment on Elastic Coefficients of Al-Cu Alloys Containing Columnar Crystals*", Zairyoshi, Vol 32, No. 352, pages 94–100 in which Yamaguchi et al used ultrasonic sonic wave velocities to determine the elastic stiffness of Al-Cu alloys containing columnar crystals. Yamaguchi et al used great care to prepare the surface of a six inch thick aluminum plate employed to conduct his research. This was done because they were making precise velocity calculations from very precise thickness measurements.

The principal object of the present invention is to provide an inexpensive, nondestructive method for the detection of twinned columnar growth (TCG) in aluminum alloys which is more convenient than prior methods.

Another object of the present invention is to inexpensively detect, locate and quantify structural anisotropies such as TCG throughout the entire cross-section of an ingot in a timely fashion.

Another object of the present invention is to provide a nondestructive method for the detection of anisotropies in as-formed aluminum pieces that is not dependent on making precise velocity measurements.

Still another object of the present invention is to provide a nondestructive method for the detection of anisotropies in as-formed aluminum pieces that is not dependent on making precise thickness measurements to calculate precise velocities.

Another object of the present invention is to provide a nondestructive method for the detection of anisotropies in as-formed aluminum pieces that can utilize rough as formed surfaces and does not require costly surface preparation.

Another object of the present invention is to provide a nondestructive method for the detection of anisotropies in as-formed aluminum pieces having cross-section of approximately two feet.

Yet another object of the present invention is to provide a nondestructive method for the detection of anisotropies in as-formed metals including aluminum alloys without the need to prepare a test surface.

Yet another object of the present invention is to provide a nondestructive method for the detection of anisotropies in as-cast aluminum ingots without the need to scalp the ingot prior to testing.

Additional objects and advantages of the invention will be more fully understood and appreciated with reference to the following description.

SUMMARY OF THE INVENTION

In accordance with the present invention, a nondestructive method for determining the presence of twinned columnar growth in the interior of an as-cast ingot, the method including the steps of: (a) forming a metal item by a method selected from the group of casting, electromagnetic casting, squeeze casting, rheocasting, compocasting, vacuum casting, slab casting, forging, extruding and rolling (b) attaching a transducer to the metal prior to working; (c) energizing the transducer to generate ultrasonic waves capable of penetrating the metal item; (d) measuring the time of flight (TOF) of ultrasonic waves through the metal item; (e) rotating the transducer approximately 90°; (f) repeating step (d); and (g) determining the difference between steps (d) and (f) to determine the presence of TCG.

In a preferred embodiment of the present invention, the step of forming metal is casting ingot of an aluminum alloy. The transducers are attached to the ingot so as to generate a wavefront normal in a direction perpendicular to the casting direction.

The transducers used in the present invention preferably generate ultrasonic waves having a frequency of greater than 0.2 MHz and less than 50 MHz. The most preferred range of frequencies is between approximately 1 MHz and approximately 20 MHz.

Preferably, a viscous coupling agent is applied to the metal item prior to attaching the ultrasonic transducer. A semi-solid coupling material may also be used, provided it is sufficiently plastic to be impressed into and form a negative of the ingot surface.

The rotation of the transducers may be accomplished manually. In addition, the rotation of the transducers need not be approximately 90°. It may be multiples of 45° which are not 180°, 360° or multiples thereof. Thus for example, the transducers may be rotated approximately 45°, 90°, 135°, 225°, 270°, 315° and multiples thereof which are not also multiples of 180° or 360°.

A second embodiment of the present invention is an improved transducer for determining the presence of twinned columnar growth in the interior of a piece of metal. The transducer unit having a base that can be rotated while it is affixed to the metal so as to rotate the polarity of the wave front penetrating the metal without changing the location of the transducer unit.

In a preferred embodiment of the second aspect of the present invention, the ultrasonic transducer is a unit of two or more stacked piezoelectric transducers. The stack may be polarized, parallel or perpendicular to the casting direction of the ingot.

The stacked piezoelectric transducers utilize an oriented crystal which is strained along a particular crystallographic axis in response to an electric field applied to the crystal (the piezoelectric effect). An electronic means permits one to change the electric field from one transducer to the next and thereby switch or rotate the direction of the ultrasonic waves used in testing. The rotation of the polarity of the wave front in this preferred embodiment of the present invention is accomplished without physically rotating the base of the transducer unit.

BRIEF DESCRIPTION OF THE DRAWINGS

Other features of the present invention will be further described or rendered obvious in the following related description of the preferred embodiment which is to be considered together with the accompanying drawings wherein like figures refer to like parts and further wherein.

MODE FOR CARRYING OUT THE INVENTION

The characteristics of ultrasonic waves are generally well understood. For example, it is known that the principal effect of stress on ultrasonic waves propagated through metallic materials occurs in the direction of material vibration or particle motion of the crystalline lattice of metallic materials. It is known, also, that X-cut crystals are suitable for use as transducers for propagating longitudinal waves to initiate vibration in the direction of propagation, while Y-cut crystals are suitable for use as transducers for propagating shear waves orthogonally related to the direction of propagation.

For the sake of convenience, transducers employed in propagating longitudinal waves are hereinafter referred to as longitudinal wave transducers while transducers employed for propagating shear waves are hereinafter referred to as shear wave transducers. The transducers used in the present invention are shear wave transducers. These shear wave transducers vibrate parallel to the surface of the ingot in an oscillating pattern similar to an electrical sander.

It is also recognized by those skilled in the art of measurement of stress in metallic bodies employing ultrasonic waves that longitudinal waves propagated along paths normally related to planes of stress tend to be unaffected by the stress while the transit time for shear waves propagated along similar paths tends to increase as tensile stress increases and decreases as compressive stress increases. Applicants have found that it is possible to obtain a difference in time values based on the orientation of crystals within the as-cast ingot and not on internal stress or external stress applied to the ingot. If the residual internal stress level in the as-cast ingot is known to be high, the ingot may have to undergo a heat treatment to reduce internal stress to a level that the method of the present invention can be used.

The term "as-cast ingot" as used herein describes ingot that has not undergone metal working stages such as rolling or roll casting. "As-cast ingot" may or may not have been subjected to a stress relieving treatments subsequent to casting.

Figure 1:
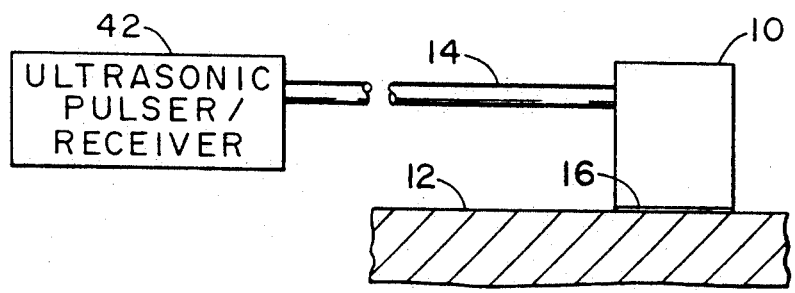
FIG. 1 is a side view of a transducer coupled to the surface of an as-cast piece of aluminum ingot.

Turning now to FIG. 1, there is illustrated a transducer 10 coupled to an as-cast piece of aluminum ingot 12. Cylindrical aluminum ingots can have a diameter of up to 42 inches. Rectangular aluminum ingots can have a thickness of up to 24 inches and a width of several feet. Transducer 10 is connected to an ultrasonic pulser/receiver 20 via cable 14.

Ultrasonic pulser/receivers are commercially available from, for example, Panametrics, Waltham, Mass. The frequency used by the ultrasonic pulser/receiver to determine the presence of TCG is limited in part by the physics of the material to be tested. Thus for example, in an as-cast aluminum ingot, the grains in the metal will determine the upper end of the range. Grain size effect the reading by making it more difficult to transmit the ultrasonic signal through the ingot. At higher frequencies the transmission is less but it is possible to get a more precise measure of the difference between the time-of-flight (TOF) readings taken with polarization parallel and perpendicular to the direction of casting. At the lower end, the sound wave is less attenuated but the precision of the measurement is compromised.

The ultrasonic pulser/receiver used in practicing the method of the present invention must be capable of generating ultrasonic waves having a frequency greater than 0.2 MHz and less than 50 MHz The most preferred range of frequencies is between approximately 1 MHz and approximately 20 MHz.

A viscous coupling agent 16 is used to couple transducer 10 to ingot 12. Coupling agent 16 is not required to practice the method of the present invention. If efficiency is not a primary concern the transducer may be dry coupled to the surface or forcibly held to the surface to be tested. In addition, lasers and electromagnetic accoustic transducers may also be used.

If a coupling agent 16 is to be used it is normally applied to the metal ingot 12 prior to attaching transducer 10 thereto. The coupling agent works best if the surface of the ingot has been degreased. The thickness of the coupling agent will vary according to the surface roughness of the ingot. A typical thickness is in the range of approximately 2 millimeters for as-cast surfaces.

The chemical composition of the coupling agent employed is not critical to practicing the present invention. However, it is preferred that coupling agent 16 have a viscosity equal to or greater than honey. A preferred viscosity for the coupling agent is greater than approximately two centipoise. The relatively high viscosity of the coupling agent used in the present invention insures that transducer 10 is rigidly attached or coupled to ingot 12 in order to inject an ultrasonic shear wave into the material.

A viscous liquid that has been successfully employed as 1 coupling agent is Panametric SWC. This material is commercially available from Panametric Inc.. A dry couplant that has been used is commercially available from Martin Marietta under the tradename of ECOU.

In operation, a cast ingot is allowed to cool to approximately room temperature so that it may be tested. Before working the metal, a coupling agent is applied to the surface of the ingot in a sufficient thickness to smooth over imperfections on the ingot surface. The transducer is then applied to the couplant.

If the surface of the ingot is "extra rough", it may be necessary to lightly scalp the surface to insure adequate coupling of the transducer.

Once the transducer is coupled to the ingot, the transducer is then connected to an ultrasonic pulser/receiver which will generate an electrical pulse which piezoelectrically generates ultrasonic mechanical waves capable of penetrating the ingot. There are many commercially available ultrasonic pulser/receiver, such as for example, Panametric Pulser 5050PR. Time-of-flight readings are then taken with polarization parallel and perpendicular to the direction of casting.

Figure 2:
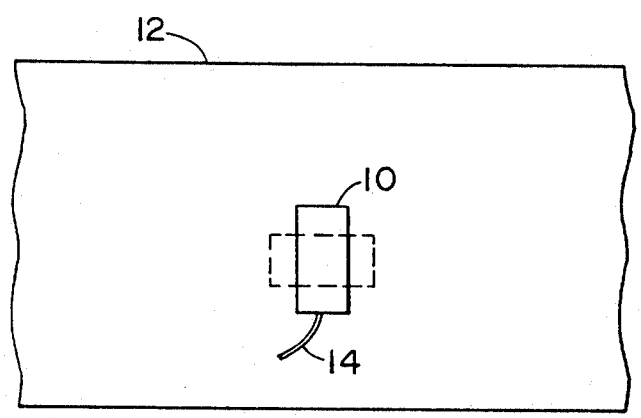
FIG. 2 is a top view of the transducer of FIG. 1 showing a second position of the transducer in shadow.

Turning next to FIG. 2, there is illustrated a top view of the transducer of FIG. 1 showing the position of transducer 10 in a first position and in a rotated second position, shown in shadow.

The time differential of round trip time-of-flight time for the wave front to pass through the cross section of the ingot and return is recorded in multiples of 100 nanoseconds. The numbers in each section were evaluated according to the following standard:

| less than 4 | Acceptable - TCG unlikely |
|---|---|
| greater than 4 | Unacceptable - TCG present |

This standard is subjective, others may choose to make the cut-off for acceptable ingots at other than a value less than 4.

After determining the likelihood of TCG, the transducer can then be disconnected and reconnected to obtain time-of-flight readings in another area. The entire process can be repeated until the entire ingot has been tested.

Figure 3:
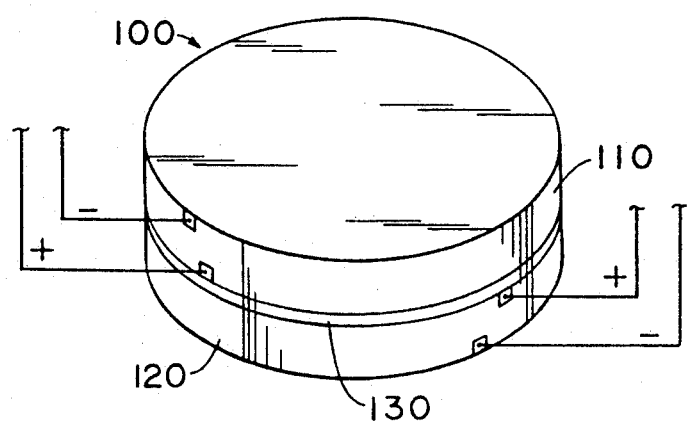
FIG. 3 is a side view of a preferred transducer for use in the present invention.

Turning next to FIG. 3, there is illustrated a preferred embodiment of the transducer unit 100 used in practicing the method of the present invention. Transducer unit 100 comprises two stacked piezoelectric transducers 110 and 120 which are separated by a layer of adherent 130. Adherent 130 which holds piezoelectric transducers 110 and 120 together. These transducers utilize an oriented crystal which is strained along a particular crystallographic axis in response to an electric field applied to the crystal (the piezoelectric effect). An electronic means permits one to change the electric field from one transducer to the next and thereby switch or rotate the direction of the ultrasonic waves used in testing. The rotation of the polarity of the wave front in this preferred embodiment of the present invention is accomplished without physically rotating the base of the transducer unit.

EXAMPLE 1

An ingot of aluminum alloy AA 5657 was cast according to accepted practices. After the ingot cooled, a transducer was attached to its surface using Panametric SWC as a coupling agent. Time-of-flight readings were taken with polarization parallel and perpendicular to the direction of casting using ultrasonic waves generated at approximately 5 MHz. The surface of the ingot was marked into sections one foot by one foot square and round trip time-of-flight readings were taken for each of the marked sections.

Figure 4:
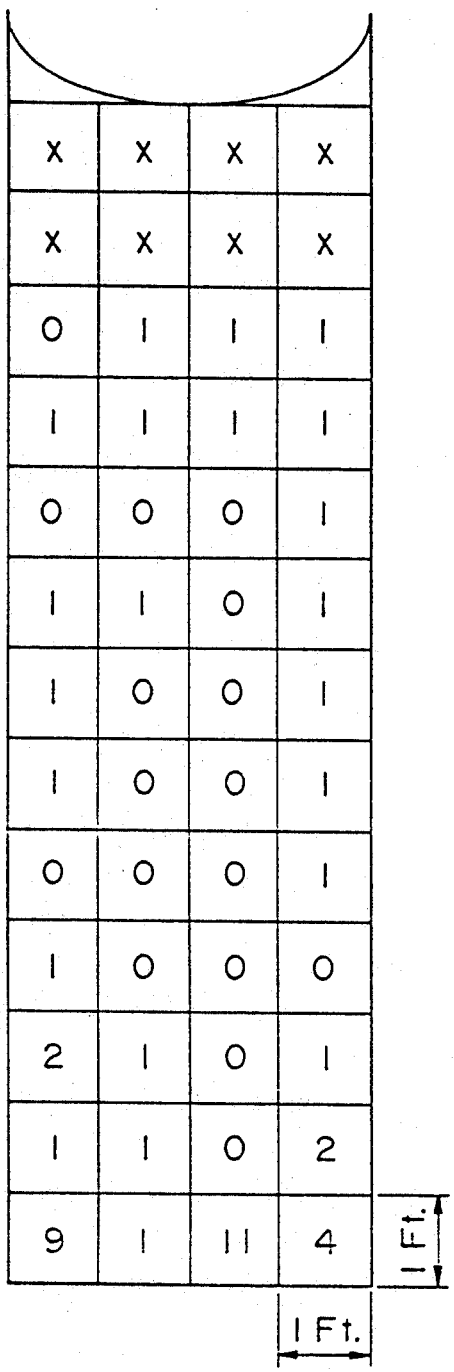
FIG. 4 is an illustration of a top view an ingot of aluminum alloy AA 5657 showing the location and magnitude of the difference in the time-of-flight readings taken with polarization parallel and perpendicular to the direction of casting.

FIG. 4 is an illustration of a top view the ingot of Example 1 showing the location and magnitude of the difference of the time-of-flight readings taken with polarization parallel and perpendicular to the direction of casting for each section. The numbers in each section represent multiples of 100 nanoseconds in the difference of round trip time-of-flight time for the wave front to pass through the cross section of the ingot and return. The numbers in each section were evaluated according to the following standard set forth above.

As can be seen from FIG. 4, TCG was only present in the first foot of the ingot. Heretofore, if one obtained results that indicated that TCG was present in an ingot, the entire ingots may have been remelted. It was simply too costly and time consuming to determine if part of the ingot is free of TCG and potentially useful for making quality product.

EXAMPLE 2

Figure 5:
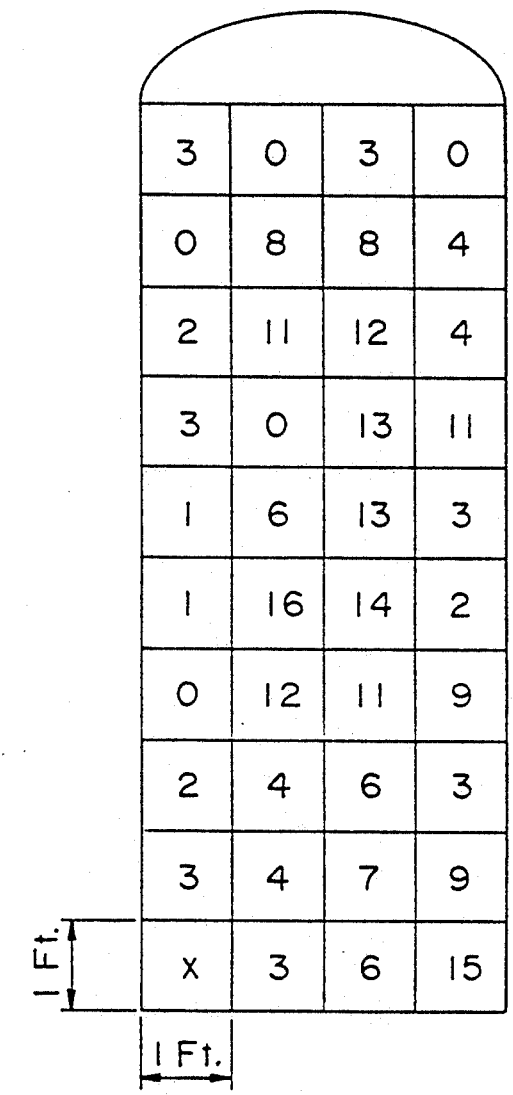
FIG. 5 is an illustration of a top view an ingot of aluminum alloy AA 5083 showing the location and magnitude of the difference in the time-of-flight readings taken with polarization parallel and perpendicular to the direction of casting.

An ingot of aluminum alloy AA 5083 was cast and tested according to the procedure of Example 1. FIG. 5 is an illustration of a top view an ingot of aluminum alloy 5083 showing the location and magnitude of the difference in the time-of-flight readings taken with polarization parallel and perpendicular to the direction of casting.

As can be seen from FIG. 5, TCG is randomly present throughout the entire ingot.

It is to be appreciated that certain features of the present invention may be changed without departing from the present invention. Thus, for example, the surface of the metal to be tested can be scalped prior to testing. "Extra rough" metal surfaces may require some scalping. However, the surfaces do not have to be polished, etched or machined so that opposite surfaces are perfectly parallel.

It is contemplated that the method and apparatus of the present invention will be valuable in the testing of alloys other than aluminum alloys. Metals suitable for testing according to the present invention include aluminum, titanium, magnesium, copper, steel, nickel, cobalt, zinc, and alloys thereof.

It is also to be appreciated that although the metal used was as-cast ingot, other fabrication methods known to the art may also be utilized. Thus, for example, the metal to be tested may be fabricated by electromagnetic casting, DC casting, squeeze casting, rheocasting, compocasting, vacuum casting, slab casting, rolling or forging. In addition, the casting technique used to form the metal objects may be carried out using mechanical, hydraulic, vacuum and/or high pressure means.

Furthermore, it is also to be appreciated that although the metal used in practicing the present invention was cooled to room temperature, this is not a critical feature of the invention. The present invention can be practiced on hot metal having a solid surface. The upper temperature limit for practicing the current invention is the solidus temperature of the alloy. The solidus temperature is a temperature below the temperature at which TCG and other anisotropies form.

In addition, it is also contemplated that angles other than parallel and perpendicular to the direction of casting may also be used in practicing the present invention. In particular, there exists good reason to believe that measurements taken 45° to the direction of casting will be especially valuable in detecting TCG.

Although the invention has been described in terms of a transducer which sits flush against the surface, an intermediate layer such as a transducer holder may also be added without departing from the invention. The use of an intermediate layer is desirable in that it prevents damage to the surface of the transducer. The intermediate layer need not have parallel surfaces. Rather, it may be wedge shaped so that the transducer generates pulses which pass through the ingot at other than perpendicular to the surface. Since TCG has been known to form parallel to the heat flow direction, a wedge that rotates the transducer might be useful.

It is to be appreciated that although the invention was described in terms of time-of-flight (TOF) measurement, the current invention is not so limited. The through time of the electrically generated pulses may also be used. This will involve coupling and rotating two transducers.

It is also to be appreciated that although the the aluminum alloys used in the Examples contained little, if any, residual internal stress, the invention is not so limited. Other alloys containing high levels of residual stress, such as for example, aluminum lithium alloys, can also be used. If the residual internal stress level in the as-cast ingot test piece is known to be high, the ingot may be subjected to any of the stress relieving treatments, for example heat treatment, prior to making the ultrasonic test.

These and other changes of the type described could be made to the present invention without departing from the spirit of the invention. The scope of the present invention is indicated by the broad general meaning of the terms in which the claims are expressed.

What is claimed is:

1. A system for detecting if anisotropic structures are present inside an as-formed metal object, said system including:
   (a) a single transducer unit for determining the presence of anisotropic structures in the interior of said metal object, said transducer unit having a base for connection to a first side of said metal object, said base being rotatable in relation to said metal object; and
   (b) an ultrasonic pulser/receiver electrically connected to said transducer unit for energizing said transducer unit to form shear waves and measuring the time of flight of said shear waves through said metal object from said first side of said metal object to a second side opposite said first side and then back again to said first side of said metal object.

2. The system of claim 1 which further comprises:
   (c) a coupling agent for coupling said transducer unit to said first side of said metal object.

3. The system of claim 2 in which said coupling agent is a viscous liquid and has a viscosity greater than 2 centipoise.

4. The system of claim 1 which further comprises:
   (c) a viscous liquid for coupling said transducer unit to said first side of said metal object.

5. The system of claim 4 in which said viscous liquid has a viscosity equal to or greater than honey.

* * * * *